(12) United States Patent
Drake et al.

(10) Patent No.: US 6,330,904 B2
(45) Date of Patent: *Dec. 18, 2001

(54) MICROWAVE-BASED PROCESS FOR DENTAL CASTING

(75) Inventors: Billy Wayne Drake; Doyle W. Hopkins, both of Charlotte, NC (US)

(73) Assignee: Micro Electronics Group Inc., Charlotte, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/251,536

(22) Filed: Feb. 17, 1999

(51) Int. Cl.⁷ ....................................................... B22C 9/02
(52) U.S. Cl. .............................. 164/35; 164/516; 164/44
(58) Field of Search ................................ 164/516, 35, 44

(56) References Cited

FOREIGN PATENT DOCUMENTS

| 56-117860 | * | 9/1981 | (JP) | 164/35 |
| 57-68244 | * | 4/1982 | (JP) | 164/35 |
| 57-72748 | * | 5/1982 | (JP) | 164/516 |
| 59-5383 | * | 2/1984 | (JP) | 164/35 |
| 1-197041 | * | 8/1989 | (JP) | 164/35 |
| 57-68243 | * | 8/1989 | (JP) | 164/35 |

\* cited by examiner

*Primary Examiner*—M. Alexandra Elve
(74) *Attorney, Agent, or Firm*—Timothy R. Kroboth

(57) ABSTRACT

A microwave-based process for dental casting includes the use of microwave radiation to obtain burnout of a wax pattern from an investment mold. Phosphate-based, thermal investment materials have been found suitable for use in the process.

18 Claims, 6 Drawing Sheets

MICROWAVE-BASED PROCESS FOR DENTAL CASTING

FIELD OF THE INVENTION

This invention relates to the use of microwave energy for making dental castings.

BACKGROUND OF THE INVENTION

Conventionally, cast metal restorations are made by a process involving embedding a wax pattern in an investment material, eliminating the wax pattern from the investment mold, and thereafter producing a metal casting from the mold. Typically, a wax or plastic sprue is attached to the wax pattern before it is invested, so that during the wax elimination step a channel known as a sprue channel, provides an escape route for molten wax and its residue during the wax elimination. More specifically, in a conventional procedure, the sprue channel provides an escape route from the investment mold that terminates near the centerpoint of the bottom surface of the investment mold.

Conventionally, the wax pattern is eliminated by burnout of the mold, and a burnout furnace having an electric muffle (or heating chamber) is used. To create an oxidizing atmosphere in the burnout furnace, an open vent hole is usually located high in the back wall of the furnace. When the wax pattern melts and burns, it leaves a residue of carbon, and at elevated temperatures, oxygen forms carbon monoxide and carbon dioxide from the carbon residue.

Thereafter, in a conventional procedure, a metal casting is made from the mold by use of a casting machine. A commonly used casting machine is a centrifugal casting machine in which the rotation is in a horizontal plane. Porcelain may be used to cover the metal casting, and ultimately a dental restoration is put into a patient's mouth. Full cast crowns are waxed to exact dimensions and are finished and polished after casting.

Different types of investment materials are known, and include thermal investments. Typically, for a thermal investment, the wax pattern is invested in a casting ring and allowed to set for a minimum of about 60 minutes before being placed in the burnout furnace. Usually, the furnace is initially at room temperature and is heated slowly during a period of about 4.5 hours to an elevated temperature of 1200° or 1600° F. To eliminate the wax pattern, this elevated temperature is generally maintained for a period of 1 hour minimum, and the total burnout time is about 270 to 280 minutes, plus about 15 minutes extra for each additional ring.

Although this conventional process is widely used and has great acceptance, an improved process for making cast metal and porcelain fused to alloy restorations is needed. For example, the conventional process, and in particular the technique for burnout of the mold, is time intensive. Benefits would be obtained by reducing the time in terms of both labor and energy savings.

SUMMARY OF THE INVENTION

In accordance with the present invention, a microwave-based process for making dental castings is provided. By the process, a wax pattern is embedded in a suitable thermal investment material conveniently with the use of a plastic former. Beneficially, the investment material is phosphate-based. Advantageously, a sprue is attached to the wax pattern before it is invested, so that during wax elimination a sprue channel provides an escape route that terminates near the bottom surface of the investment mold.

Thereafter, the wax pattern and investment mold are subjected to microwave radiation in an enclosed burnout chamber under conditions sufficient to eliminate the wax pattern by burnout of the investment mold. Beneficially, the microwave operates at no less than about 700 watts. Furthermore, advantageously the walls for the burnout chamber form an opening for a door for access to the chamber interior, and gas flow into and out of the chamber occurs between the door and the door opening.

After burnout of the investment mold, a metal casting is made from the mold. Thereafter, the metal casting is cleaned and prepared for porcelain application, or finished and polished in the case of a full cast crown.

BRIEF DESCRIPTION OF THE DRAWINGS

Reference is now made to the accompanying drawing, which forms a part of the specification of the present invention.

DETAILED DESCRIPTION OF THE INVENTION

Figure 1:
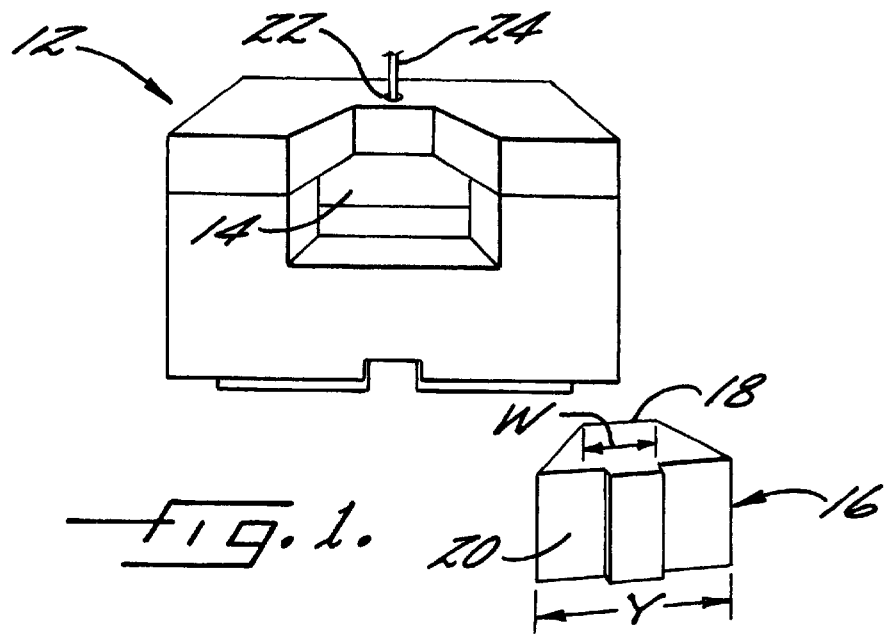
FIG. 1 is a perspective view of a prior art burnout chamber useful in the process of the present invention, with the chamber door removed.

As indicated above, the process of the present invention is advantageously based upon the use of microwave radiation to obtain burnout of an investment mold. Surprisingly, it has been found that investment molds processed using microwave radiation for wax pattern elimination, produce metal castings of improved quality compared to metal castings from investment molds processed using a conventional electric burnout furnace. Beneficially, improved fit and smoother cast have been found, with resultant labor savings. Furthermore, it has been found that the particular thermal investment material selected can be significant to the consistency of results. Moreover, it has been found that the combination of investment material selected, microwave wattage output and other burnout conditions including burnout chamber flow-through rate, can in addition provide improved integrity of investment molds after burnout, and metallurgical improvement in metal castings made from investment molds, as well as a remarkable reduction in the time necessary for burnout. Advantageously, inclusions are reduced, alloy structure is improved, and bond enhancement is found. Undesirable inclusions in metal castings include gas bubbles, debris and carbon.

In accordance with the process of the present invention, a wax pattern is embedded in a suitable thermal investment material. Useful thermal investment materials will typically include quartz, crystobalite and magnesium oxide, as well as phosphate in the form of a phosphate salt. Although the amount of quartz and crystobalite may vary, about 25 to 50 wt. % has been found to be advantageous in an investment material. Phosphate-based thermal investment materials may include monoammoniumdihydrogen phosphate as the phosphate salt; however, thermal decomposition of this ingredient at 300 to 400° C. by separation of ammonia, is known. It is believed that freedom of an investment material from an ingredient producing an ammonia decomposition product, is preferred in the inventive process. Other components of thermal investment materials may be aluminum oxide and inorganic color.

To embed the wax pattern, the investment material powder is mixed with a liquid, typically colloidal silicic acid in water, and the result is a plaster-like mold which forms under the development of heat. Useful liquids include a solution of about 20 to 50% colloidal silicic acid in water.

A useful investment material is sold under the trademark Bellavest-T, and is constituted as follows (wt %):

60–90% quartz and cristobalite (fine dust)
5–15% monoammoniumdihydrogenphosphate
5–15% magnesia oxide
0–30% aluminum oxide
0–4% inorganic color such as zinc oxide, titanium oxide, graphite.

To make a plaster-like mold, this powder is mixed with a liquid of 35–45% colloidal silicic acid in water.

A preferred investment material for use in the inventive process, is sold under the trademark Heravest, and includes quartz and cristobalite (25 to 50 wt %), and magnesium oxide, as well as phosphate. As stated, freedom from an ingredient producing an ammonia decomposition product, is beneficial in the inventive process. To make a plaster-like mold, the Heravest powder is mixed with a liquid of 20–50% colloidal silicic acid in water.

The relative proportions of powder and liquid mixed to make an investment mold generally will depend upon the alloy to be cast, and thus is determined based upon factors including the appropriate thermal expansion. Typically, to provide for relatively more thermal expansion, relatively more liquid is used, and to provide for less thermal expansion, relatively less liquid is used. In addition, consideration should be given to ambient humidity and temperature, as well as to altitude. Useful formulations for making Heravest investment molds using Heravest powder, 20–50% colloidal silicic acid in water, and distilled water are in the Table.

TABLE

| powder | silicic acid liquid | dist. water | total liquid |
|---|---|---|---|
| NOBLE AND HIGH NOBLE CERAMIC ALLOYS | | | |
| 90 g | 15 ml | 6.5 ml | 21.5 ml |
| 60 g | 8.5 ml | 4.5 ml | 13 ml |
| NOBLE AND HIGH NOBLE CROWN & BRIDGE ALLOYS | | | |
| 90 g | 12.5 ml | 9 ml | 21.5 ml |
| 60 g | 8 ml | 5 ml | 13 ml |
| BASE ALLOYS | | | |
| 90 g | 18 ml | 3.5 ml | 21.5 ml |
| 60 g | 12 ml | 1 ml | 13 ml |

Mixing of the powder and liquid is conventionally carried out under vacuum conditions until a uniform mixture results. Thereafter, the wax pattern and sprue are embedded in the resulting investment mold. The setting time varies depending upon the investment powder and liquid used, and processing conditions including the ambient temperature. Thereafter, glaze is beneficially removed from the top of the investment mold.

Figure 4:
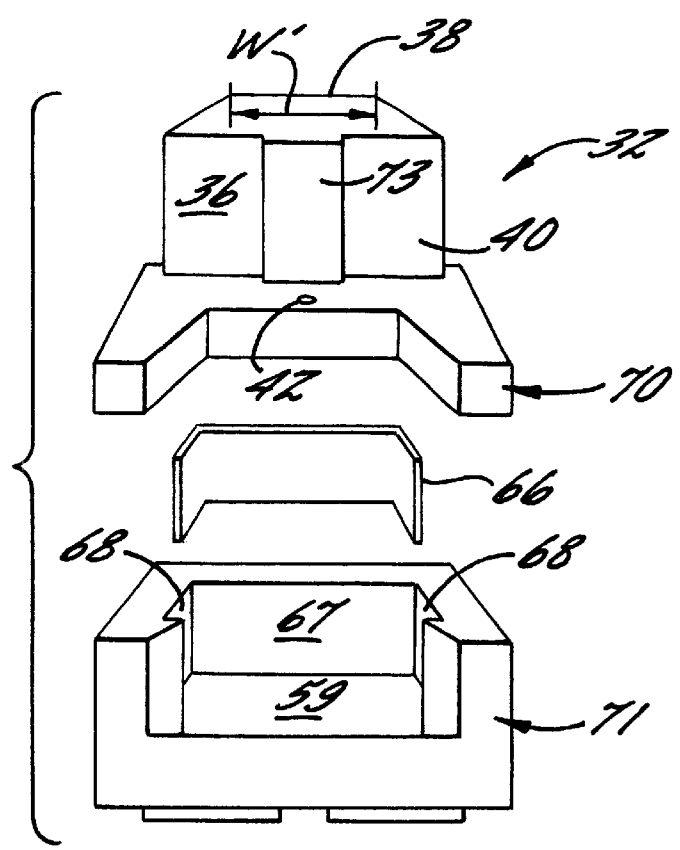
FIG. 4 is an exploded view of the burnout chamber of the furnace of FIG. 2.
Figure 2:
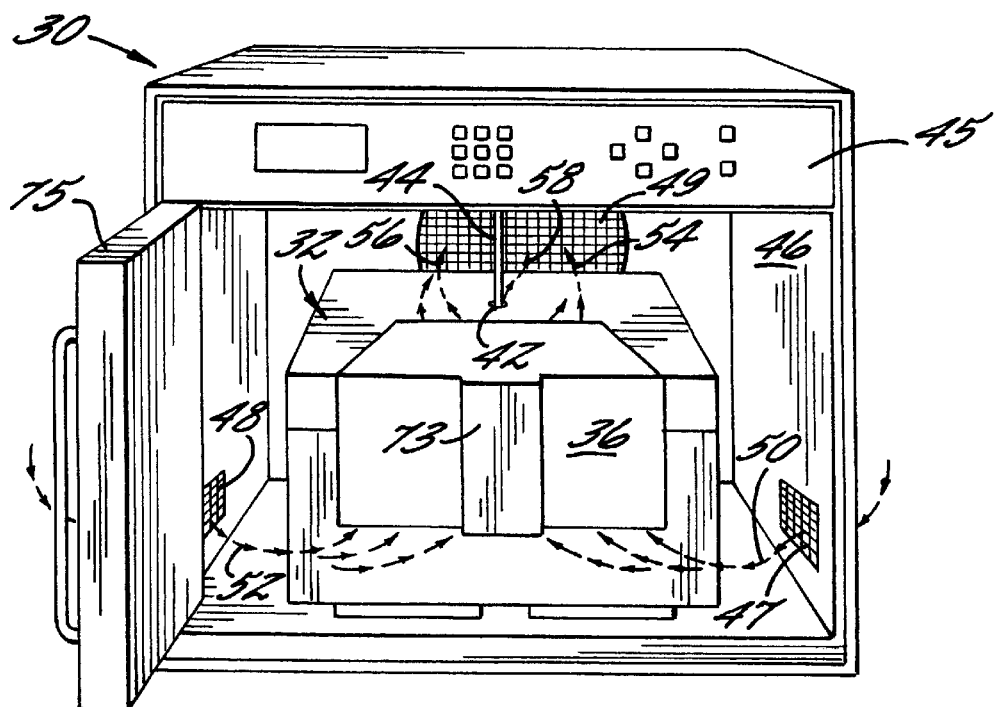
FIG. 2 is a perspective view of a preferred microwave burnout furnace useful in the process of the present invention, in which gas flow into and out of the burnout chamber is illustratively shown.
Figure 3:
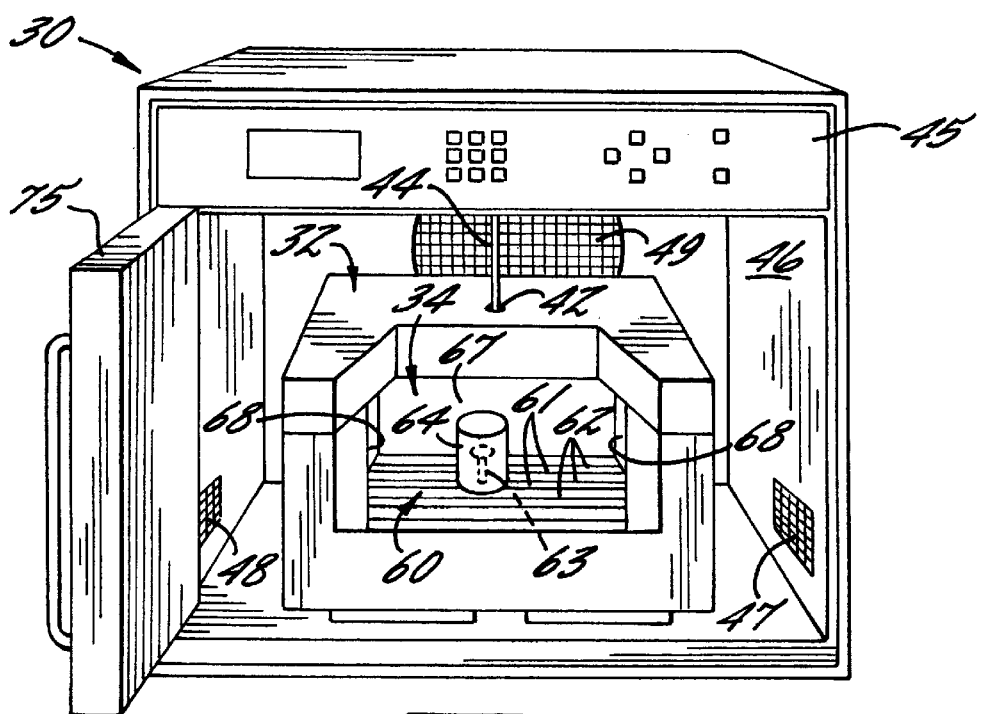
FIG. 3 is a similar view of the furnace of FIG. 2 with the chamber door removed.

In accordance with the process of the present invention, the wax pattern and investment mold are subjected to microwave radiation in an enclosed burnout chamber under conditions sufficient to obtain burnout of the mold. A useful chamber 12 of this type is illustrated in FIG. 1, and is commercially available from CEM Corporation of Matthews, N.C. as part of a microwave apparatus sold under the name MAS 7000. A preferred microwave apparatus 30 and burnout chamber 32 for the inventive process, is shown in FIGS. 2 to 4. In either case, the microwave apparatus does not include an isolator, and the burnout chamber is made of microwave transmissive (preferably essentially transparent to microwave radiation), heat resistant material of low thermal conductivity, and in particular an open celled ceramic foam, preferably an open celled fused quartz foam. This type material helps to maintain the temperature uniform throughout the burnout chamber cavity, designated 14 in FIG. 1 and 34 in FIG. 3.

Beneficially, the walls of the burnout chamber form an opening for a removable door, designated 16 in FIG. 1 and 36 in FIGS. 2 and 4, for access to the chamber cavity. The door matches in shape the wall opening, and is likewise beneficially made of such material. The door includes an inner wall, designated 18 in FIG. 1 and 38 in FIG. 4, of less width than an outer wall, designated 20 in FIG. 1 and 40 in FIG. 4. The inner wall of the door, when the door is in place, completes the interior wall structure of the chamber cavity.

The burnout chamber also includes a vertical bore, designated 22 in FIG. 1 and 42 in FIGS. 2–4, for a thermocouple probe, designated 24 in FIG. 1 and 44 in FIGS. 2 and 3, which is connected to a temperature controller (not shown) which operates a microwave power control (not shown) which controls the magnetron (not shown) as appropriate. Operation of microwave apparatus 30 is controlled by a panel 45. Beneficially, a temperature sensor (not shown) for switching off the magnetron when the temperature within walled microwave retainer chamber 46 is sensed as exceeding a certain temperature limit, is located above the burnout chamber. To this end, the ceiling panel (not shown) of retaining chamber 46 includes an opening (not shown) for the sensor, and the opening and sensor are located above the removable door.

Beneficially, in accordance with the inventive process, the microwave power is not less than 700 watts. Preferably, the microwave is capable of operating at 800 watts or more, and it is highly preferable that the microwave is capable of operating at 900 watts or more, but typically less than 1100 watts.

Referring to the preferred apparatus of FIGS. 2 to 4, and in particular to FIG. 2, gas flow through retaining chamber 46 and burnout chamber 32 during burnout is represented by arrows. Air enters retaining chamber 46 through grill openings 47 and 48 in the side walls, which openings are located near the bottom of the chamber, and passes upwardly and around burnout chamber 32, after which it passes out through opening or duct 49, from whence it is discharged through an air exhaust duct preferably to a fume hood or in other permissible manner. When door 36 is in place in the door opening, clearance between the door opening and the door allows passage of air into the cavity of the burnout chamber, as represented by arrows 50 and 52. Although the arrows indicate air flow under the door, air also enters the burnout chamber cavity through the lower portions of the side clearances between the door and the door opening. Similarly, combustion gases from burnout and air leave the burnout chamber cavity as represented by arrows 54 and 56, and through the upper portions of the side clearances. Conveniently, the previously mentioned temperature sensor is located directly above the location from which combustion gases vent as depicted in FIG. 2, so that heat from combustion gases is quickly sensed. Arrow 58 represents the passage of combustion gases and air out of the burnout chamber cavity through the clearance between thermocouple probe 44 and the wall of bore 42. The gas exhausted from the burnout chamber cavity passes through exhaust duct 49 to a suitable hood or other discharge means. Conveniently, a blower (not shown) assists outflow through exhaust duct 49, and the blower is turned on and off in response to the temperature within microwave retaining chamber 46.

Referring particularly to FIG. 3, a channeled plate heating element 60 with a plurality of spaced apart channels 61, is beneficially disposed in the bottom 59 (shown in FIG. 4) of the burnout chamber cavity. Plate 60 includes a plurality of spaced apart raised areas 62 between which channels 61 which run side to side in the cavity, are located. In accordance with the process, a wax pattern and sprue 63 embedded in an investment mold 64, are beneficially disposed during burnout on the channeled plate. During burnout, molten wax flows through the sprue channel into the channels of the channeled plate and heat from the channeled plate benefits volatilization and combustion of the wax.

Referring particularly to FIG. 4, a heating element 66 (omitted from FIG. 3 for clarity of FIG. 3) is positioned within the burnout chamber cavity and partially covers back wall 67 and side walls 68 of the cavity. By comparison, a heating element (not shown) for burnout chamber 12 of FIG. 1 is of considerably greater mass and completely covers the interior vertical walls of chamber 12 other than inner wall 18 of removable door 16. Accordingly, heating element 66 provides less load, and is approximately one-third less load. Conveniently, the burnout chamber, and in particular burnout chamber 22, includes separable upper and lower sections 70,71 for introduction and removal of this heating element. Advantageously, channeled plate 60 and this heating element are made of a microwave absorptive material that is capable of being heated to a burnout temperature by microwave radiation.

Fluid flow into and out of the burnout chamber may be controlled by adjusting the removable door to increase or decrease the clearance between the door and the door opening, by use of a door handle, designated 73 in FIGS. 2 and 4. Fan or blower speed for regulating inflow through grill openings 47,48 and outflow through duct 49, can also be changed to adjust the fluid flow. Beneficially, in accordance with the inventive process, door 36 has an inner wall width w' (shown in FIG. 4) of at least about 20% greater extent compared to width w of door 16, with the extent preferably being at least about 45% greater. Otherwise, the burnout chambers and burnout chamber cavities of FIGS. 1 and 4 are substantially identical to one another in dimensions. Benefits include increased fluid flow into and out of chamber cavity 34 compared to flow into and out of cavity 14 of burnout chamber 12. It is believed that it is advantageous to provide for relatively greater fluid flow into and out of the burnout chamber cavity to take into account more rapid combustion and volatilization when operating at 800 or 900 watts or more.

Conditions affecting mold burnout include time, temperature and the fluid flow rate into and out of the burnout chamber. As can be understood, a relatively higher temperature requires relatively less time, and a relatively higher fluid flow rate requires relatively less time. Thus, microwave power of about 800 watts or more and the wider door of FIGS. 2 and 4 are preferred. Conveniently for relatively faster burnout using a HERAVEST-like investment material, the temperature of the burnout chamber at the time the investment mold is placed in the chamber interior, is at least about 600 or 1000, advantageously 800 or 1200° F. Typically, burnout temperatures of about 1200, 1300 or 1600° F. will be used in the inventive process.

EXAMPLE 1

A wax pattern and sprue were embedded in a phosphate-based, thermal investment material commercially available from BEGO Bremer Goldschlagerei Wilh. Herbst GmbH & Co. of Bremen, Germany, under the trademark Bellavest-T. The investment material was mixed in accordance with manufacturer's instructions depending upon the amount of powder used and taking into consideration thermal expansion, ambient temperature and humidity, and altitude. A plastic former of appropriate size and vacuum mixing were used. The setting time was 60 minutes, after which glaze was removed from the top of the ring.

Thereafter, referring again to the prior art furnace 12 of FIG. 1, the investment mold was placed in the interior furnace 12 of a microwave apparatus commercially available from CEM Corporation of Matthews, N.C. under the name MAS 7000, and having a microwave power of 740 watts, a heating element that completely covers the interior vertical walls of furnace 12 other than inner wall 18 of removable door 16, and a blower for the microwave retaining chamber outlet duct that is turned on when the temperature in the microwave retaining chamber reaches about 212° F. Door 16 (inner wall 18 having a width w of 4.5", and outer wall 20 having a width y of 6.5") of the interior furnace was then put into place. With the microwave operating at full power, the interior furnace was heated from about ambient temperature to 500° F., and after a hold time of 10 to 12 minutes, second stage heating to 1600° F. was carried out.

Once 1600° F. was reached, the mold was removed from the microwave apparatus to cast immediately a metal casting. To this end, the hot mold was placed in a centrifugal casting machine with rotation in the horizontal plane. Using the procedure of this Example, metal castings were formed from noble ceramic alloys and base alloys. By modification of the procedure whereby the second stage heating was to 1300° F., metal castings were formed from high noble ceramic alloys. By modification of the procedure whereby the second stage heating was to 1300° F. and the temperature was thereafter allowed to cool to 1000° F. prior to placing the hot mold in the casting machine, metal castings were formed from noble and high noble crown and bridge alloys.

It was found that these metal castings were of improved quality compared to metal castings from investment molds processed using a conventional electric burnout furnace. Typically, the castings had a better fit and were smoother castings.

EXAMPLE 2

A wax pattern and sprue were embedded in Bellavest-T investment material as in Example 1, with the sprue positioned to provide a sprue channel terminating near the centerpoint of the bottom surface of the investment mold. After glaze removal from the top of the ring, referring again to FIGS. 2 to 4, the investment mold was placed on channeled plates in cavity 34 of burnout chamber 32 of microwave apparatus 30 having a microwave power of 925 watts, heating element 66 in cavity 34, and a blower for microwave retaining chamber outlet duct 49 that is turned on when the temperature in microwave retaining chamber 46 exceeds 95° F., in particular reaches 122° F. Removable door 36 of the burnout chamber (inner wall 38 having a width w' of 6.5", and outer wall 40 having a width of 8.5") was then put into place, and microwave door 75 was closed. With the microwave operating at full power, the burnout chamber was heated from about ambient temperature to 500° F., and after a hold time of 8 to 10 minutes, second stage heating to 1600° F. was carried out.

Once 1600° F. was reached, the mold was removed from the microwave apparatus to cast immediately a metal casting. To this end, the hot mold was placed in a centrifugal casting machine with rotation in the horizontal plane. Using the procedure of this Example, metal castings were formed from noble ceramic alloys and base alloys. By modification of the procedure whereby the second stage heating was to 1300° F., metal castings were formed from high noble ceramic alloys. By modification of the procedure whereby the second stage heating was to 1300° F. and the temperature was thereafter allowed to cool to 1000° F. prior to placing the hot mold in the casting machine, metal castings were formed from noble and high noble crown and bridge alloys.

It was found that these metal castings were of improved quality compared to metal castings from investment molds processed using a conventional electric burnout furnace. Typically, the castings had a better fit and were smoother castings. In the case of metal castings from noble and high noble crown bridge alloys, the cooling to 1000° F. was found to produce a smoother quality casting compared to a casting made without this cooling step.

EXAMPLE 3

A wax pattern and sprue were embedded in a phosphate-based, thermal investment mold commercially available from Heraeus Kulzer GmbH of Hanau, Germany, under the trademark HERAVEST, with the sprue positioned as in Example 2. For casting a noble ceramic alloy, the investment powder, silicic acid liquid and distilled water were mixed in accordance with the Table depending upon the amount of powder to be used. A plastic former of appropriate size, and 120 second mechanical spatulation under vacuum were used. The setting time was 45 minutes, after which glaze was removed from the top of the ring.

Thereafter, the investment mold was placed on channeled plates in cavity 34 of burnout chamber 32 of microwave apparatus 30 used in Example 2. The removable door was put into place and microwave door 75 was closed. With the microwave operating at full power, the burnout chamber was heated from 1200° F. to 1600° F. The time to reach 1600° F. was approximately 14 minutes.

Once 1600° F. was reached, the mold was removed from the microwave apparatus to cast immediately a metal casting. To this end, the hot mold was placed in a centrifugal casting machine with rotation in the horizontal plane. Using the procedure of this Example, metal castings were also formed from base alloys. By modification of the procedure whereby the burnout chamber was heated from 800° F. to 1300° F., metal castings were formed from high noble ceramic alloys using the formulations of the Table, and by modification of the procedure whereby the burnout chamber was heated from 800° F. to 1200° F., metal castings were formed from noble and high noble crown and bridge alloys using the formulations of the Table.

Although a relatively lower initial temperature for a burnout chamber can be used, time is saved by beginning with a relatively higher initial temperature.

However, use of an initial temperature in excess of 1200° F., can be deleterious. For instance, investment mold cracks were found when an initial temperature of 1400° F. was used.

Investment molds made in accordance with this Example were surprisingly of improved integrity after burnout, and metal castings were surprisingly of improved metallurgical quality compared to metal castings from investment molds processed using a conventional electric burnout furnace. Also, a very high consistency of results was found. In addition, the castings had a better fit and were smoother castings.

Figure 5A:
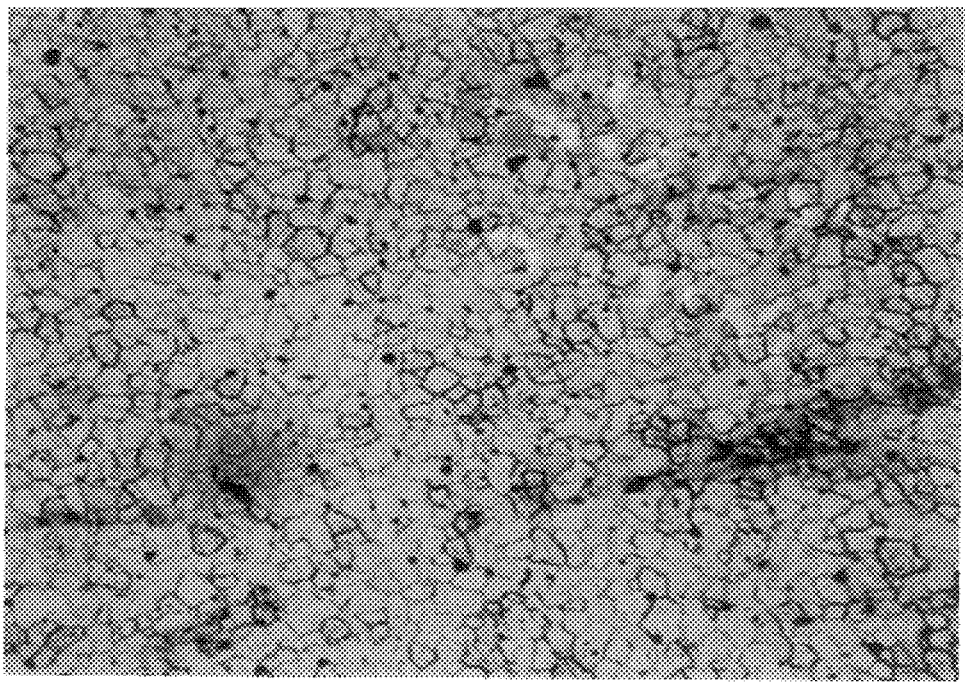
FIGS. 5A and 5B, 6A and 6B, 7A and 7B, and 8A and 8B are photographs showing metallurgical differences visible in cross-section under magnification, between metal castings made in accordance with the inventive process and metal castings made using a conventional burnout furnace.
Figure 5B:
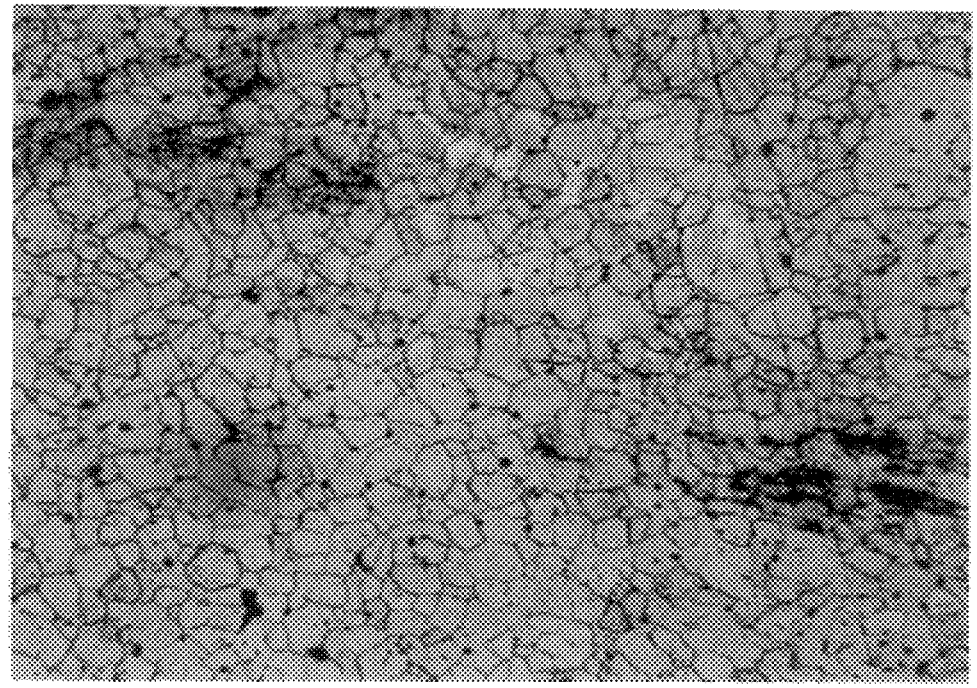
Figure 6A:
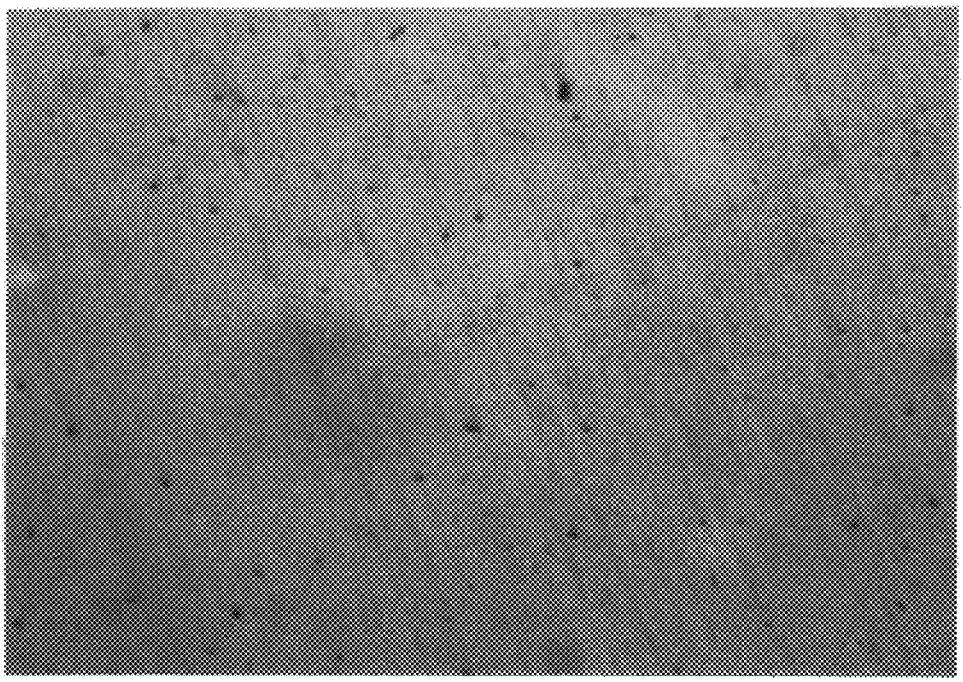
Figure 6B:
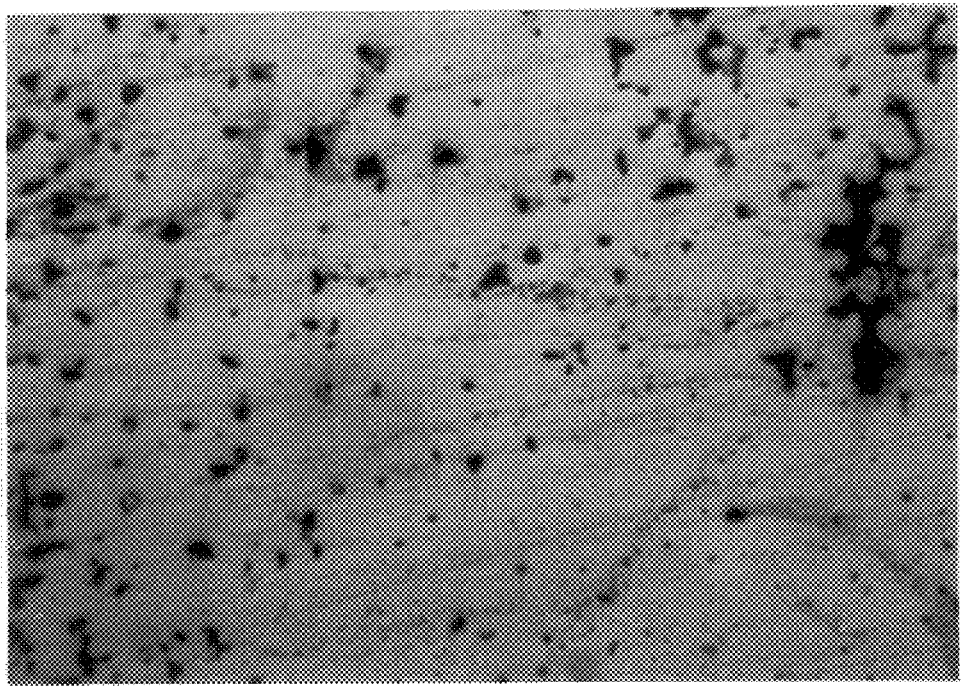

FIGS. 5A and 5B (noble ceramic alloy) demonstrate a significant reduction in grain size during grain reformation in FIG. 5A for a metal casting made generally using the procedure of this Example compared to a metal casting made using a conventional burnout furnace. In addition, FIGS. 6A and 6B (noble ceramic alloy) demonstrate a significant reduction in inclusions in FIG. 6A for the metal casting of FIG. 5A compared to the inclusions shown in FIG. 6B for the metal casting of FIG. 5B. Like results were found for high noble ceramic alloys.

Figure 7A:
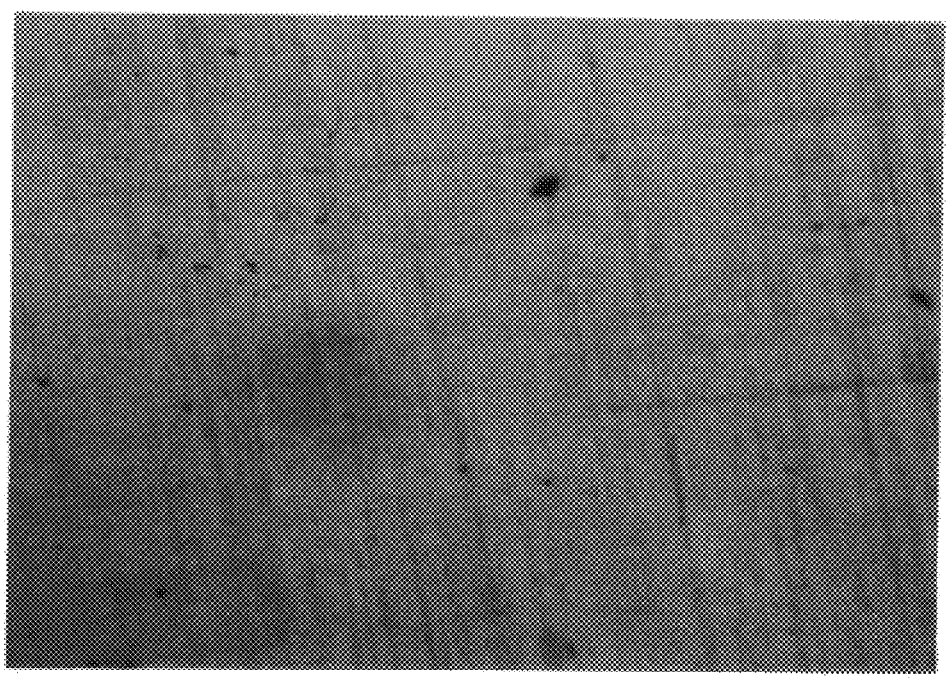
Figure 7B:
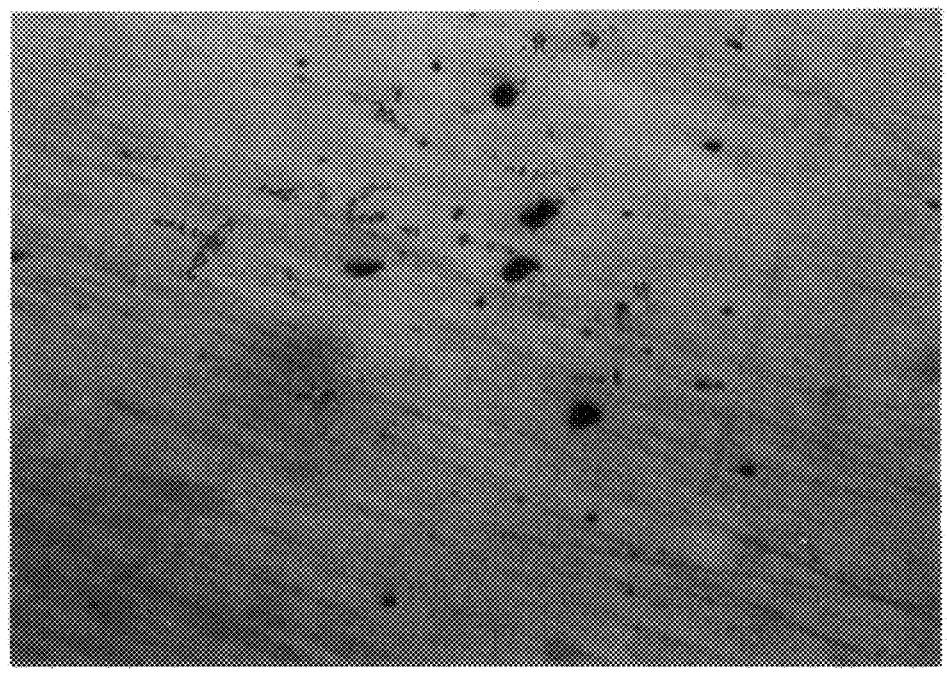
Figure 8A:
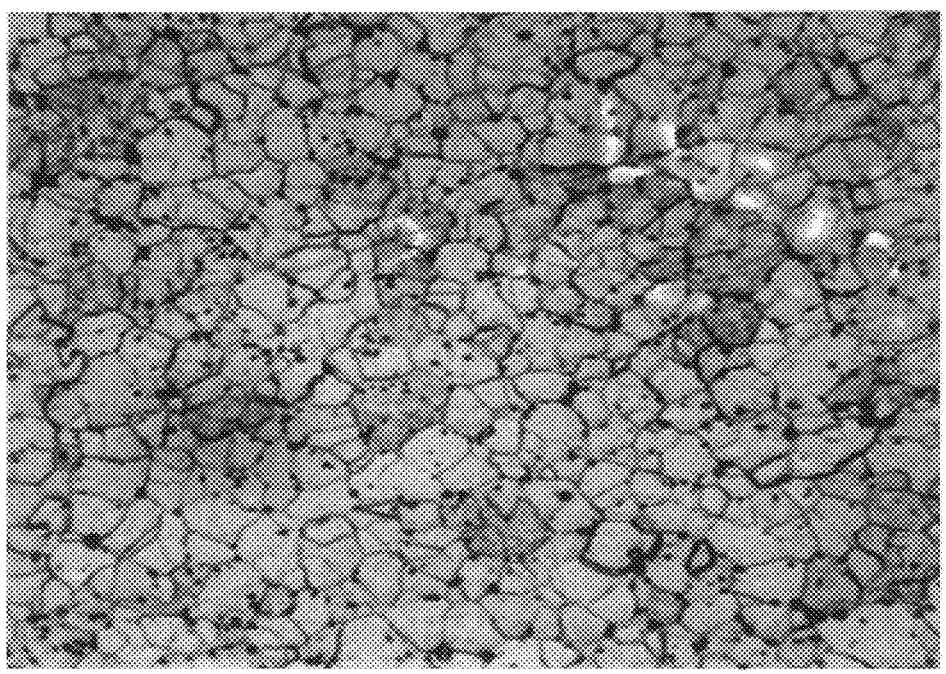
Figure 8B:
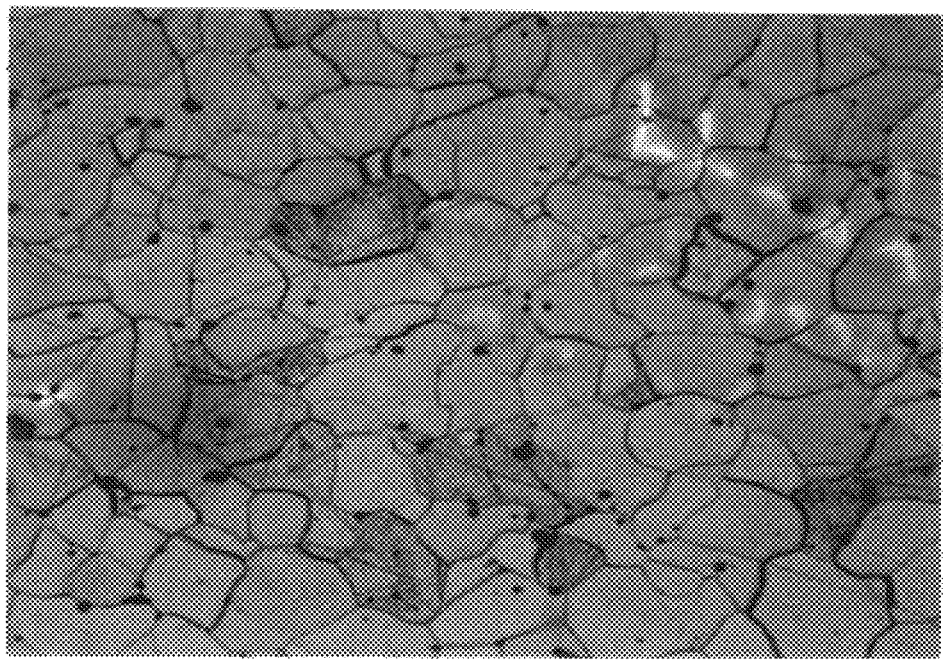

Similar results are shown in FIGS. 7 and 8 (high noble crown and bridge alloy) for a metal casting made generally using the procedure of this Example (7A,8A: significant reduction in grain size, significant reduction in inclusions) compared to a metal casting made using a conventional burnout furnace (7B,8B: larger grain size, more inclusions).

The present invention may be carried out with various modifications without departing from the spirit or essential attributes thereof, and accordingly, reference should be made to the appended claims, rather than to the foregoing specification as indicating the scope of the invention.

What is claimed is:

1. A microwave-based process for burnout of a dental casting mold comprising embedding a wax pattern in a suitable thermal investment material to make an investment mold with said wax pattern embedded therein; and eliminating said wax pattern from said investment mold by subjecting said wax pattern and investment mold to microwave radiation under conditions sufficient to obtain burnout of said mold, wherein said microwave is operating at about 700 watts or more, wherein said wax pattern and investment told are enclosed in a microwave transmissive burnout chamber of low thermal conductivity, said burnout chamber being disposed within a microwave retaining chamber, wherein a heat-emissive element is disposed within said burnout chamber, and said investment mold and said heat-emissive element are positioned relative to one other during the mold burnout such that said heat-emissive element is beneath said investment mold and molten flow from an escape channel provided in said investment mold during the mold burnout occurs onto said heat-emissive element, which is adapted to assist said molten flow from said escape channel, wherein fluid flow into and out of said burnout chamber occurs during the mold burnout, and wherein said burnout chamber includes walls forming an opening for a door for access to the chamber interior and fluid flow occurs between said door and said walls.

2. The process of claim 1, wherein said thermal investment material is free of an ingredient producing an ammonia decomposition product during burnout of the mold.

3. The process of claim 1, wherein said thermal investment material comprises phosphate, and about 25 to 50 wt. % quartz and crystobalite.

4. The process of claim 3, wherein said thermal investment material further comprises magnesium oxide.

5. The process of claim 1, wherein said fluid flow comprises gas flow, wherein said door has an inner wall width w' providing an improved burnout chamber flow through rate, and wherein said microwave is operating at about 800 watts or more during the mold burnout.

6. The process of claim 1, wherein said fluid flow comprises gas flow, wherein said door has an inner wall width w' of about 45% greater extent for improved fluid flow, and wherein said microwave is operating at about 900 watts or more during the mold burnout.

7. The process of claim 1, wherein fluid flow out of said retaining chamber occurs during the mold burnout, and said fluid flow out of said retaining chamber is mechanically enhanced when the temperature within said retaining chamber exceeds 95° F.

8. The process of claim 1, wherein said burnout chamber is at a temperature selected from at least 600° F. and at least 1000° F. at the time said wax pattern and investment mold are placed in said chamber interior.

9. The process of claim 8, wherein said temperature is elected from about 800° F. and 1200° F.

10. The process of claim 1, wherein the embedding step occurs outside of said microwave retaining chamber.

11. A dental casting process in accordance with claim 5, further comprising after the mold burnout, producing a dental casting from the mold.

12. The process of claim , wherein a temperature of from about 1200° F. to 1600° F. is used for the mold burnout, and the mold is at a temperature of from 1000° F. to 1600° F. when metal for the casting step is added to the mold.

13. The process of claim 1, wherein said heat-emissive element is a channeled plate, and said investment mold is positioned, during the mold burnout, on said channeled plate and said escape channel faces said channeled plate.

14. The process of claim 1, wherein said wax pattern is attached to a sprue positioned to provide said escape channel, and said sprue is a wax sprue, and said molten flow from said escape channel is molten wax.

15. The process of claim 1, wherein said microwave is operating at about 740 watts or more during the mold burnout.

16. The process of claim 1, wherein said microwave is operating at about 800 watts or more during the mold burnout.

17. The process of claim 1, wherein said microwave is operating at about 900 watts or more during the mold burnout.

18. The process of claim 1, wherein said conditions comprise a burnout temperature of 1200° F. or more.

* * * * *